United States Patent
Yamagata et al.

(10) Patent No.: US 11,642,337 B2
(45) Date of Patent: May 9, 2023

(54) THERAPEUTIC AGENT FOR MENTAL RETARDATION OR AUTISM

(71) Applicant: TOKYO METROPOLITAN INSTITUTE OF MEDICAL SCIENCE, Tokyo (JP)

(72) Inventors: Kanato Yamagata, Tokyo (JP); Tadayuki Shimada, Tokyo (JP); Hiroko Sugiura, Tokyo (JP); Shin Yasuda, Tokyo (JP)

(73) Assignee: TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 0 days.

(21) Appl. No.: 16/762,179

(22) PCT Filed: Nov. 7, 2018

(86) PCT No.: PCT/JP2018/041393
§ 371 (c)(1),
(2) Date: May 7, 2020

(87) PCT Pub. No.: WO2019/093389
PCT Pub. Date: May 16, 2019

(65) Prior Publication Data
US 2020/0360363 A1 Nov. 19, 2020

(30) Foreign Application Priority Data
Nov. 8, 2017 (JP) .............................. JP2017-215726

(51) Int. Cl.
*A61K 31/4545* (2006.01)
*A61K 31/4709* (2006.01)

(52) U.S. Cl.
CPC ...... *A61K 31/4545* (2013.01); *A61K 31/4709* (2013.01)

(58) Field of Classification Search
CPC .................. A61K 31/4545; A61K 31/4709
See application file for complete search history.

(56) References Cited

FOREIGN PATENT DOCUMENTS

| JP | 2013-533288 | * | 8/2013 |
|---|---|---|---|
| WO | WO 01/64252 A2 | | 9/2001 |
| WO | WO 2010/057006 A9 | | 5/2010 |
| WO | WO 2012/016021 A2 | | 2/2012 |
| WO | WO 2015/164862 A1 | | 10/2015 |
| WO | 2017/170981 | * | 10/2017 |
| WO | WO 2017/170981 A | | 10/2017 |

OTHER PUBLICATIONS

Wiznitzer, J Child Neurology, VOl 19(9), Sep. 2004, 675-679. (Year: 2004).*
Waltereit, Behav Genet, 2011, vol. 41, 364-372. (Year: 2011).*
Ropers, Current Opinion in Genetics Development, 2008, vol. 18, 241-250. (Year: 2008).*
Shree, Learning Community, vol. 7(1), 201, 9-20. (Year: 2016).*
Sugiura, J Neurosci 2022; 10.1523/JNEUROSCI.0449-21.2022. (Year: 2022).*
Hovrath, J neurosci, 2019, vol. 39(13), 2542-2561. (Year: 2019).*
Schwartzer, Transi Psychiatry, 2013, e240; doi10.1038/tp.2013.16 (Year: 2013).*
Nuytens, Neurobiology of Disease, vol. 51, 2013, 144-151. (Year: 2013).*
Crino et al., "The Tuberous Sclerosis Complex," The New England Journal of Medicine (2006), vol. 355, pp. 1345-1356.
International Search Report dated Jan. 22, 2019, in PCT/JP2018/041393.
Yasuda et al. "Activation of Rheb, but not of mTORCI, impairs spine synapse morphogenesis in tuberous sclerosis complex," Sci. Rep, (2014), vol. 4, pp. 1-8.
Basso et al., "The Farnesyl Transferase Inhibitor (FTI) SCH66336 (lonafarnib) Inhibits Rheb Farnesylation and mTOR Signaling," The Journal of Biological Chemistry, vol. 290, No. 35, Sep. 2, 2005, pp. 31101-31108.
Extended European Search Report for European Application No. 18875048.3, dated Jul. 30, 2021.
Sabatini et al., "Treatment of Neurofibromatosis Type 1," Curr Treat Options Neurol, vol. 17, No. 26, 2015 (published online Apr. 29, 2015), pp. 1-11.
Villani et al., "Syndromes Predisposing to Pediatric Central Nervous System Tumors: Lessons Learned and New Promises," Curr Neurol Neurosci Rep, vol. 12, 2012 (published online Dec. 29, 2011), pp. 153-164.

* cited by examiner

*Primary Examiner* — D Margaret M Seaman
(74) *Attorney, Agent, or Firm* — Birch, Stewart, Kolasch & Birch, LLP

(57) ABSTRACT

A novel therapeutic agent effective for the treatment of intellectual disability or autism is disclosed. The therapeutic agent for intellectual disability or autism contains, as an active component(s), at least one selected from the group consisting of tipifarnib and lonafarnib. Examples of the intellectual disability include memory impairment. Examples of the memory impairment include memory impairment caused by abnormality of the Tsc1 gene and/or Tsc2 gene, and epilepsy-induced memory impairment. Also provided is a method of treating intellectual disability or autism, comprising administering an effective amount of at least one selected from the group consisting of tipifarnib and lonafarnib to a patient with intellectual disability or autism.

15 Claims, 3 Drawing Sheets

THERAPEUTIC AGENT FOR MENTAL RETARDATION OR AUTISM

TECHNICAL FIELD

The present invention relates to a therapeutic agent for intellectual disability or autism.

BACKGROUND ART

Intellectual disability is a condition in which the cognitive ability remains at a low level due to intellectual functional disorder that occurs during a developmental stage. Since there is no therapeutic agent at present, supports from the viewpoint of rehabilitation, education, and welfare are required. Autism develops by about 3 years old. It is a disorder of behavior characterized in (1) difficulty in establishment of social relationships with other people; (2) retardation of language development; and (3) restricted interests with specific matters. These are assumed to be due to functional impairment in the central nervous system caused by a certain factor.

Patent Document 1 describes a particular azaquinoline derivative. The azaquinoline derivative is described to be effective for the treatment of a number of diseases including autism and temper tantrums.

On the other hand, tipifarnib and lonafarnib are known to be useful as anticancer drugs (for example, Patent Document 2). However, effectiveness of these agents for the treatment of intellectual disability or autism is not known at all.

PRIOR ART DOCUMENTS

Patent Documents

[Patent Document 1] JP 2012-508768 A
[Patent Document 2] JP 2003-525255 A

Non-patent Document

[Non-patent Document 1] Crino, P. B., K. L. Nathanson, and E. P. Henske, The tuberous sclerosis complex. N Engl J Med, 2006. 355(13): p. 1345-56

SUMMARY OF THE INVENTION

Problems to be Solved by the Invention

An object of the present invention is to provide a novel therapeutic agent effective for the treatment of intellectual disability or autism.

Means for Solving the Problems

Since intellectual disability and autism often develop in association with each other, it is assumed that these two pathological conditions share a common pathogenic mechanism. In view of this, the present inventors searched for diseases that genetically cause these pathogenic conditions, and focused on tuberous sclerosis. Tuberous sclerosis is a phacomatosis showing multiple hamartomas in the whole body, and accompanied by intractable epilepsy, mental retardation, and autism as central nervous system symptoms (Non-patent Document 1). Since Tsc1 or Tsc2 is known to be the causative gene of tuberous sclerosis, their knockout mice can be expected as disease models of both intellectual disability and autism.

In the present invention, model mice of tuberous sclerosis, and mice showing intellectual disability and autism-like behavioral abnormality due to other causes were prepared, and their behavioral abnormality was first observed. As a result, the present inventors revealed for the first time that tipifarnib and lonafarnib, which have been studied as anticancer drugs, are extremely effective for the intellectual disability and the autism-like behavioral abnormality, thereby completing the present invention.

More specifically, the present invention provides a therapeutic agent for intellectual disability or autism, comprising, as an active component(s), at least one selected from the group consisting of tipifarnib and lonafarnib. The present invention also provides a method of treating intellectual disability or autism, comprising administering an effective amount of at least one selected from the group consisting of tipifarnib and lonafarnib to a patient with intellectual disability or autism. The present invention also provides at least one compound selected from the group consisting of tipifarnib and lonafarnib, for the treatment of intellectual disability or autism.

Effect of the Invention

The present invention provided a therapeutic agent effective for the treatment of intellectual disability or autism for the first time.

MODE FOR CARRYING OUT THE INVENTION

Figure 1:
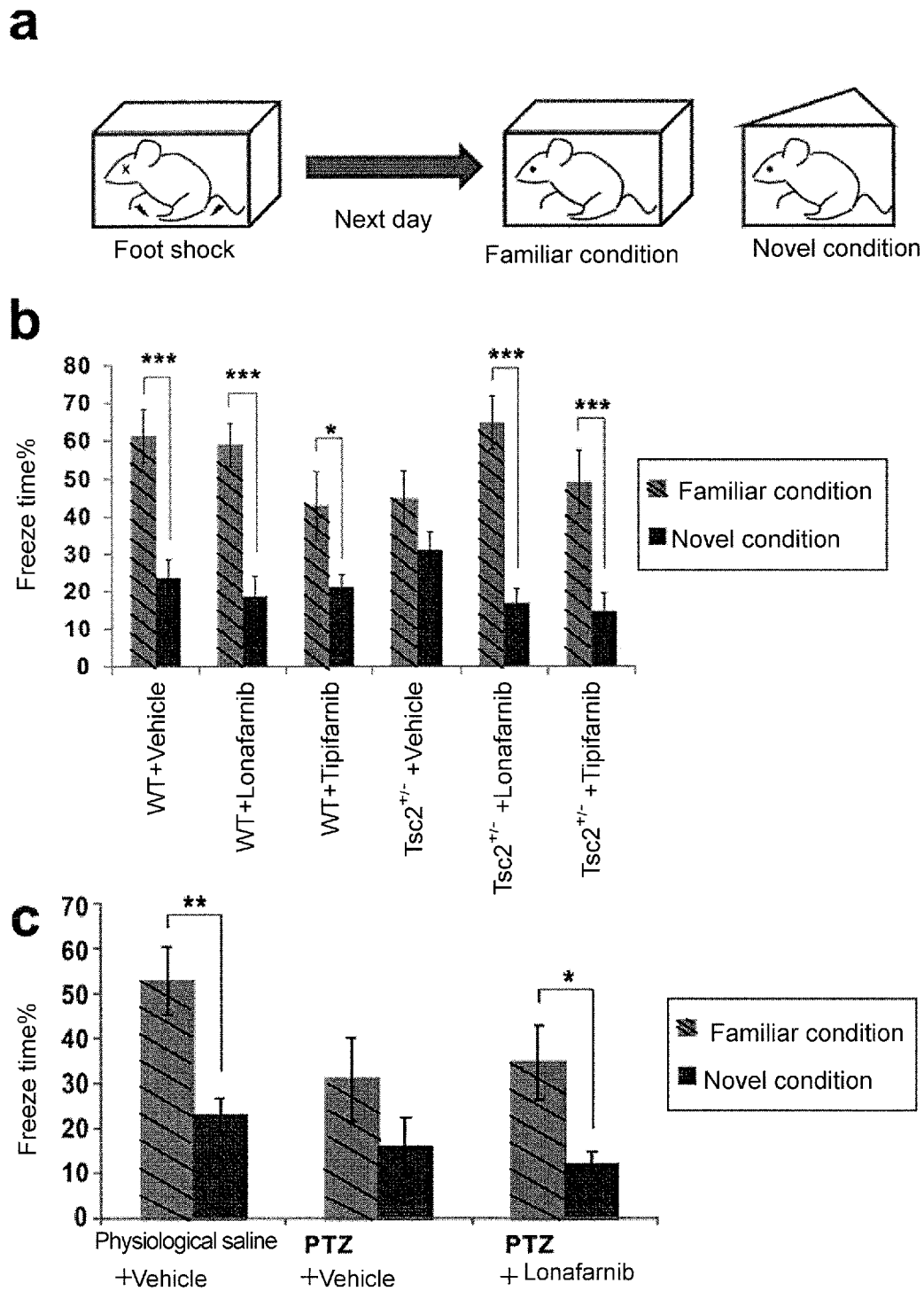
FIG. 1 is a diagram illustrating the result of the contextual fear discrimination test carried out in Example 1 described below, which shows the effect of the therapeutic agent of the present invention. Panel a is a schematic diagram of the contextual fear discrimination test. Panel b is a diagram illustrating the result of measurement of the freeze time, which shows abnormality of contextual fear memory in Tsc2$^{+/+}$ mice and recovery therefrom by administration of the therapeutic agent of the present invention. Panel c is a diagram illustrating the result of measurement of the freeze time, which shows abnormality of contextual fear memory in mice to which pentylenetetrazol was administered, and recovery therefrom by administration of the therapeutic agent of the present invention.

As described above, the therapeutic agent of the present invention contains, as an active component(s), at least one selected from the group consisting of tipifarnib (6-[(R)-amino(4-chlorophenyl)(1-methyl-1H-imidazol-5-yl)methyl]-4-(3-chlorophenyl)-1-methyl-2(1H)-quinolinone) and lonafarnib ((11R)-5,6-dihydro-3,10-dibromo-8-chloro-11-[1-[1-oxo-2-(1-carbamoyl-4-piperidinypethyl]-4-piperidinyl]-11H-benzo[5,6]cyclohepta[1,2-b]pyridine, 4-[2-[4-[(11R)-8-chloro-3,10-dibromo-6,11-dihydro-5H-benzo[5,6]cyclohepta[1,2-b]pyridine-11-yl]-1-piperidinyl]-2-oxoethyl]-1-piperidinecarboamide). These agents per se are known and commercially available. The commercially available products may be used. These agents may be used either individually or in combination.

As will be concretely described in the following Examples, the above active components exhibited excellent therapeutic effects on memory impairment in model animals of tuberous sclerosis prepared by knock-out of the TSC2 gene, and model animals of epilepsy-induced memory impairment prepared by administration of pentylenetetrazol, which is a convulsant. The above active components also showed excellent therapeutic effects on model animals of autism prepared by administration of kainic acid, which is an epilepsy-inducing agent. Based on these experimental results, it was confirmed that the above active components are effective for the treatment of intellectual disability, especially memory impairment, in particular, memory impairment caused by abnormality of the Tsc1 gene and/or Tsc2 gene, and autism.

The above active components may be orally administered, or may be parenterally administered by, for example, subcutaneous, intradermal, intramuscular, intravenous, rectal, transdermal, intraperitoneal, or intraocular administration.

The dose of the active components is appropriately set depending on the conditions such as the symptoms, age, body weight, and the like of the patient. The dose (total dose, in cases where both components are used in combination) is usually about 75 mg to 200 mg, especially about 100 mg to 150 mg, in terms of the daily dose per kg body weight of the patient.

The active components may be formulated by an ordinary formulation method, and may be administered as an oral formulation such as a tablet, powder, ball, granule, capsule or syrup, or as a parenteral formulation such as an injection solution, liniment, patch, suppository, or eye drop.

The present invention will now be described more concretely by way of Examples. However, the present invention is not limited to the following Examples.

EXAMPLES

Example 1

1. Method
(1) Animals

Tsc2$^{+/-}$ mice were prepared by breeding/crossing according to a known method (Kobayashi, T., et al., Renal carcinogenesis, hepatic hemangiomatosis, and embryonic lethality caused by a germ-line Tsc2 mutation in mice. Cancer Res, 1999. 59(6): p. 1206-11). Model mice of memory impairment different from tuberous sclerosis were prepared by 10 times of administration of pentylenetetrazol (35 mg/kg, i.p. (intraperitoneal administration)), and mice exhibiting abnormality of social behavior were prepared by single administration of kainic acid (1.5 mg/kg, i.p.) at one week old.

(2) Contextual Fear Discrimination Test

A contextual fear discrimination test (Auerbach, B. D., E. K. Osterweil, and M. F. Bear, Mutations causing syndromic autism define an axis of synaptic pathophysiology. Nature, 2011. 480(7375): p. 63-8.) was carried out to measure the contextual fear memory of mice. More specifically, each mouse was placed in a cage for application of foot shock (FS), and FS was applied to the mouse. On the next day, the mouse was returned to the same cage (familiar condition), and the freeze time was measured (FIG. 1a). In order to investigate the effect of tipifarnib or lonafarnib (which may be hereinafter simply referred to as "active component"), a vehicle (carboxymethyl cellulose) and the active component were orally administered to mice, and FS was applied to each mouse 6 hours later. On the next day, the mouse was returned to the same cage to compare the freeze time. A control experiment was also carried out by measuring the freeze time for cases where the mouse was placed in a different cage (novel condition) on the next day of the FS (FIG. 1a).

(3) Three-Chamber Test

Figure 2:
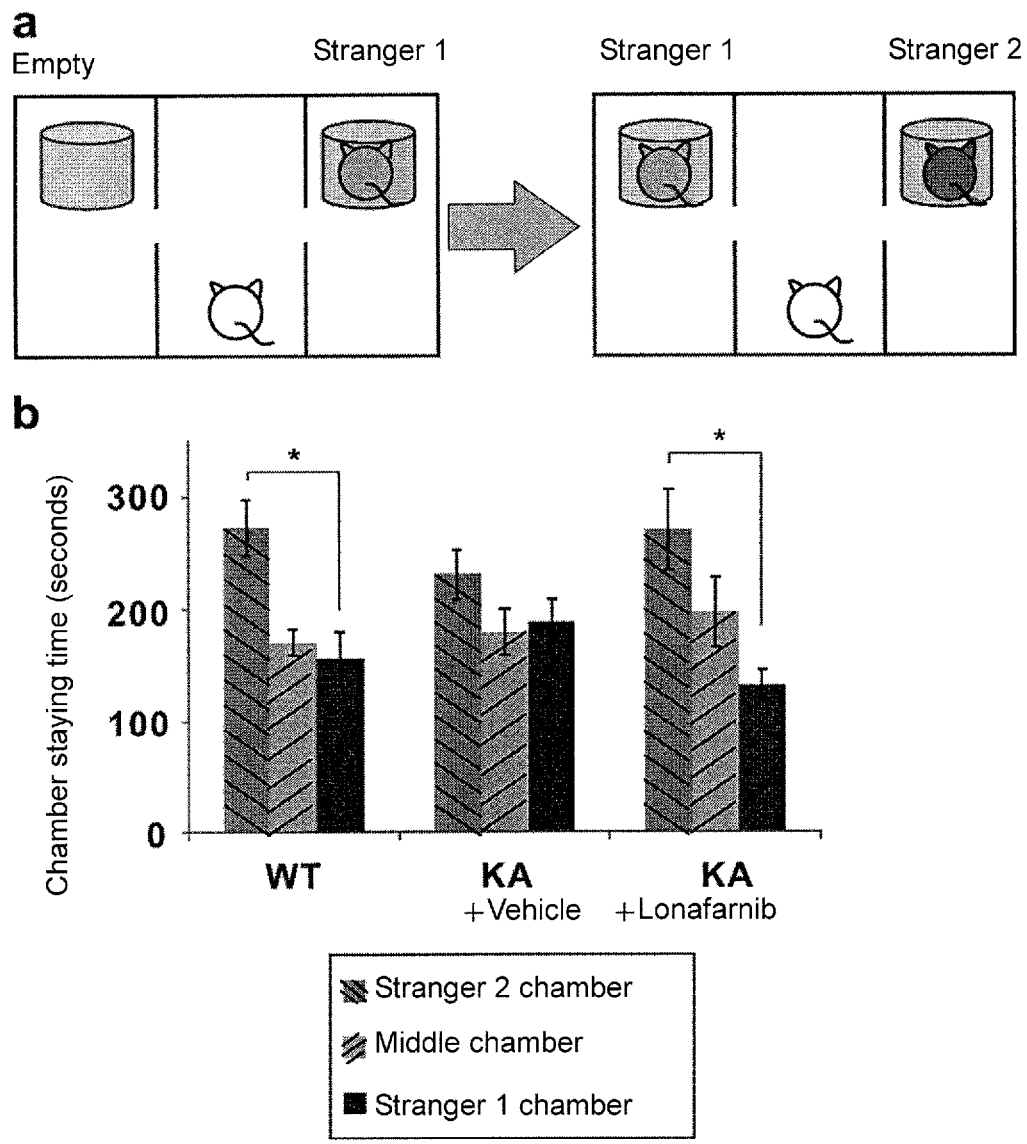
FIG. 2 is a diagram illustrating the result of the three-chamber experiment carried out in Example 1 described below, which shows the effect of the therapeutic agent of the present invention on autism. Panel a is a schematic diagram of the three-chamber experiment. Panel b is a diagram illustrating the result of measurement of the staying time in each chamber, which shows autism-like behavioral abnormality due to administration of kainic acid and recovery therefrom by administration of the therapeutic agent of the present invention.

By a three-chamber test, social interaction was investigated. This was carried out using an experiment device having three separated chambers between which a mouse can move freely. First, a cage containing a mouse (stranger 1 mouse) was placed in one chamber, and an empty cage was placed in another chamber (FIG. 2a). The subject mouse was placed in the middle chamber, and the length of time when the mouse stayed in each chamber (the chamber staying time in the figure, expressed in (s): seconds) was measured. Subsequently, the mouse (stranger 1 mouse) in the first cage was transferred to the empty cage, and another mouse (stranger 2 mouse) was placed in the cage that became empty (FIG. 2a). Thereafter, the length of time when the subject mouse stayed in the chamber of the first mouse (stranger 1 chamber) and the length of time when the subject mouse stayed in the chamber where the new mouse was staying (stranger 2 chamber) were measured and compared.

(4) Primary Culture of Hippocampal Neurons

The hippocampus was removed from Tsc2$^{+/-}$ mice on Day 0 or Day 1 after birth, and reacted in Hank's buffer supplemented with 0.25% trypsin at 37° C. for 10 minutes. After washing, the cells were suspended, and cultured using Neurobasal medium with B27 supplement at 37° C. at 5% $CO_2$. Two days before fixation, a vehicle (DMSO) and the active component (2 μM) were added to the culture liquid. For forced gene expression, Lipofectamine 2000 was used.

(5) Immunocytostaining

The cultured neurons were fixed with 4% paraformaldehyde. After blocking of the fixed neurons with a buffer containing 10% goat serum, they were reacted with a primary antibody. A fluorescent secondary antibody was then used to label the target protein. The labeled neurons were observed using LSM780, manufactured by Carl Zeiss.

2. Results
(1) Effect on Memory Impairment Caused by Tsc2 Gene Abnormality

In order to investigate the effect of the active component on intellectual disability, first, an experiment was carried out using Tsc2$^{+/-}$ mice, which exhibit abnormality of contextual fear memory. Six hours before FS, lonafarnib (40 mg/kg) or tipifarnib (40 mg/kg) was orally administered to the Tsc2$^{+/-}$ mice, and contextual fear memory was investigated (FIG. 1a). On the next day, the mice were returned to the box in which the FS was applied, and the freeze time was measured. All groups of the wild type (WT) retained memory of the FS applied on the previous day, and exhibited increases in the freeze reaction. In contrast, the vehicle administration group of the Tsc2$^{+/-}$ mice exhibited no increase in the freeze reaction, and it was therefore thought that these mice did not remember the box in which the FS was applied (FIG. 1b). However, the groups in which lonafarnib or tipifarnib was administered exhibited increases in the freeze behavior, indicating recovery of the memory (FIG. 1b). Thus, it was revealed that single administration of the active component enables improvement of memory impairment in tuberous sclerosis.

(2) Effect on Epilepsy-Induced Memory Impairment

In order to investigate whether the active component is effective also in a case other than the memory impairment due to tuberous sclerosis, preparation of mice with a different kind of memory impairment was attempted. Pentylenetetrazol, which is a convulsant, was administered 10 times to mice to cause epileptic seizure continuously. As a result of investigation of the contextual fear memory of these mice in the same manner as described above, they were found to exhibit remarkable memory impairment. In view of this, the effect of the active component on the memory impairment of these mice was also investigated. By single administration of lonafarnib (40 mg/kg, i.p.), the pentylenetetrazol-induced memory impairment could also be improved (FIG. 1c). From this result, the active component was found to have an action which improves not only tuberous sclerosis, but also epilepsy-induced memory impairment.

(3) Effect on Autism

Using model mice exhibiting autism-like behavioral abnormality, the effect of the drug was investigated (FIG. 2a). For preparation of a model exhibiting abnormality of social behavior, kainic acid (1.5 mg/kg) was injected to mice one week after birth, and the mice were grown for two months thereafter, followed by performing a three-chamber test. When a stranger 1 mouse and a stranger 2 mouse were present, wild-type mice approached the stranger 2. In contrast, the mice to which kainic acid was administered during the neonatal period did not show a significant difference between the staying times in the chambers of the stranger 1 and the stranger 2 (FIG. 2b). Thus, these mice were thought to have abnormality of social behavior. In view of this, single administration of lonafarnib (40 mg/kg, i.p.) to these mice was performed, and a three-chamber test was carried out. As a result, the staying time in the chamber of the stranger 2 (time spent in chamber) was significantly longer, indicating normal social behavior (FIG. 2b). From these results, the active component was found to have an action which also improves abnormality of social behavior (autism) in a case other than tuberous sclerosis.

(4) Effect on Abnormality of Synapse Formation

Figure 3:
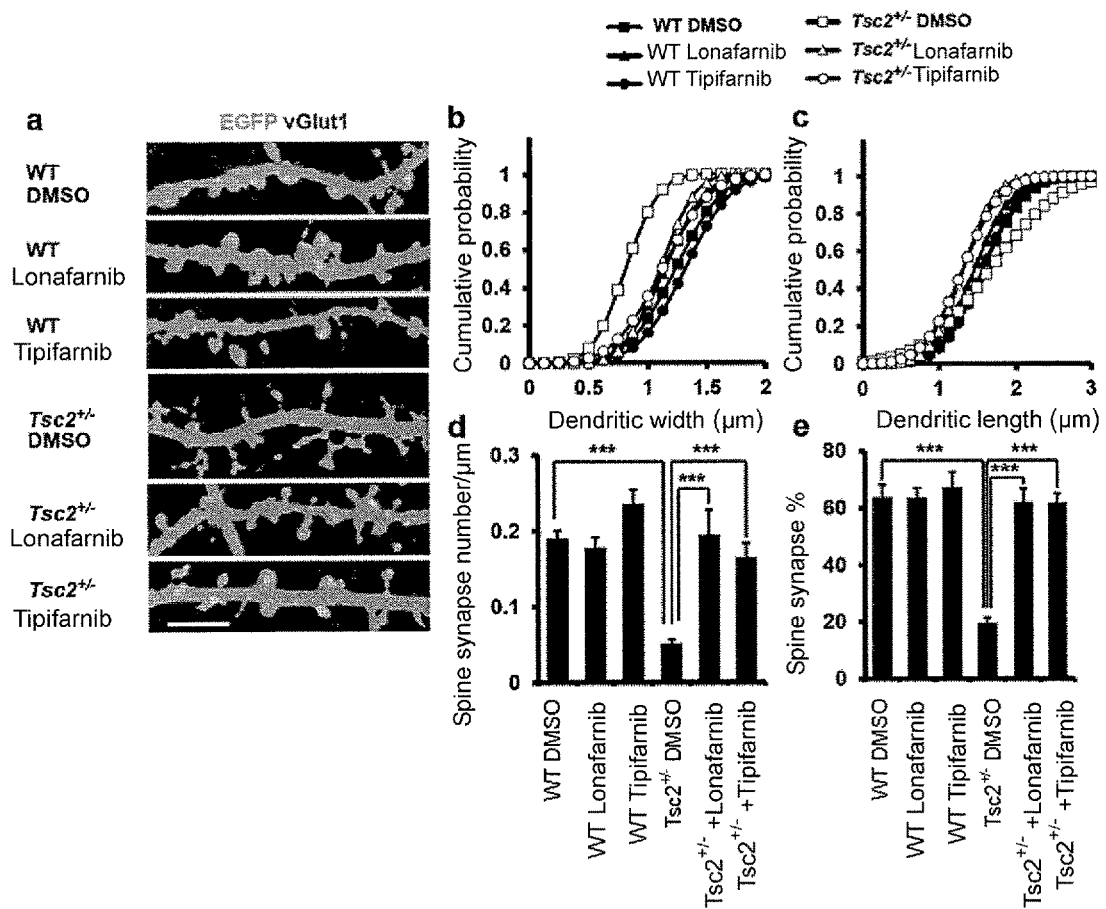
FIG. 3 is a diagram illustrating morphological abnormality found in dendritic spines of primary cultured hippocampal neurons of Tsc2 mutant mice and the effect of the therapeutic agent of the present invention as observed in Example 1 described below. Panel a is a diagram illustrating the result of administration of the two kinds of therapeutic agents of the present invention (lonafarnib and tipifarnib) to primary cultured hippocampal neurons of the wild type (WT) and the Tsc2 mutant (Tsc2$^{+/-}$) for 3 days followed by staining with GFP and a vGlut1 antibody (marker of excitatory synapses). Panel b is a diagram illustrating the result of measurement of the dendritic width of Tsc2$^{+/-}$ neurons. Panel c is a diagram similarly illustrating the result of measurement of the dendritic length. Panel d is a diagram illustrating the result of measurement of the spine synapse number. Panel e is a diagram illustrating the result of measurement of the spine synapse ratio.

The effect of the active component on abnormality of the synapse formation in the model of tuberous sclerosis was investigated. Hippocampal neurons from Tsc2$^{+/-}$ mice were subjected to primary culture, and the morphology of the neurons on Day 21 of the culture was compared with the wild type. In contrast to the wild type, which showed formation of typical mushroom-shaped spines, the Tsc2$^{+/-}$ mice showed no formation of dendritic spines, and showed the elongated immature morphology called filopodia (FIG. 3a-c). As a result of an immunostaining study of vGlut1 to see whether excitatory synapses were formed, it was found that no synapse formation occurred on the filopodia of the Tsc2$^{+/-}$ mice (FIG. 3a, d). On the other hand, excitatory synapses were directly formed on the dendrites, and exhibited the morphology of shaft synapses (FIG. 3a, e). In view of this, a vehicle or the active component (2 μM) was added to the culture liquid of Tsc2$^{+/-}$ neurons. Two days later, the neurons were fixed, and their morphology was observed. As a result, due to the treatment with the active component, the neurons exhibited the same spine morphology as the wild type, and showed formation of spine synapses exhibiting staining of vGlut1 correspondingly to the spines (FIG. 3a-e). From these results, it was found that, in tuberous sclerosis, administration of the active component causes normalization of synapses.

Example 2

1. Animals

In order to obtain a model of tuberous sclerosis exhibiting abnormality of social behavior, GFAP-Cr mice, which show astrocyte-specific Cre expression, were crossed with Tsc1$^{fl/fl}$ mice, to prepare GFAP-Cre; Tsc1$^{fl/fl}$ (GFAP-Tsc1 cKO) mice. More specifically, first, a model mouse of tuberous sclerosis exhibiting abnormality of social behavior was prepared. As a result of crossing of various Cre driver mice with Tsc1$^{fl/fl}$ mice, it was found that abnormality of social behavior can be seen in GFAP-Cre; Tsc1$^{fl/fl}$ (GFAP-Tsc1 cKO) mice. These mice were obtained by crossing of GFAP-Cre mice, which show astrocyte-specific Cre expression.

2. Preparation and Administration of Drugs

A suspension of 4 mg/ml lonafarnib or tipifarnib (using 1 w/v % CMC, 0.9 w/v % NaCl, and 5 v/v % DMSO as a vehicle) was prepared and orally administered at 40 mg/kg. A solution of 2 mg/ml pentylenetetrazol (PTZ) (using 0.9 w/v % NaCl as a vehicle) was prepared and intraperitoneally administered.

3. Results

Figure 4:
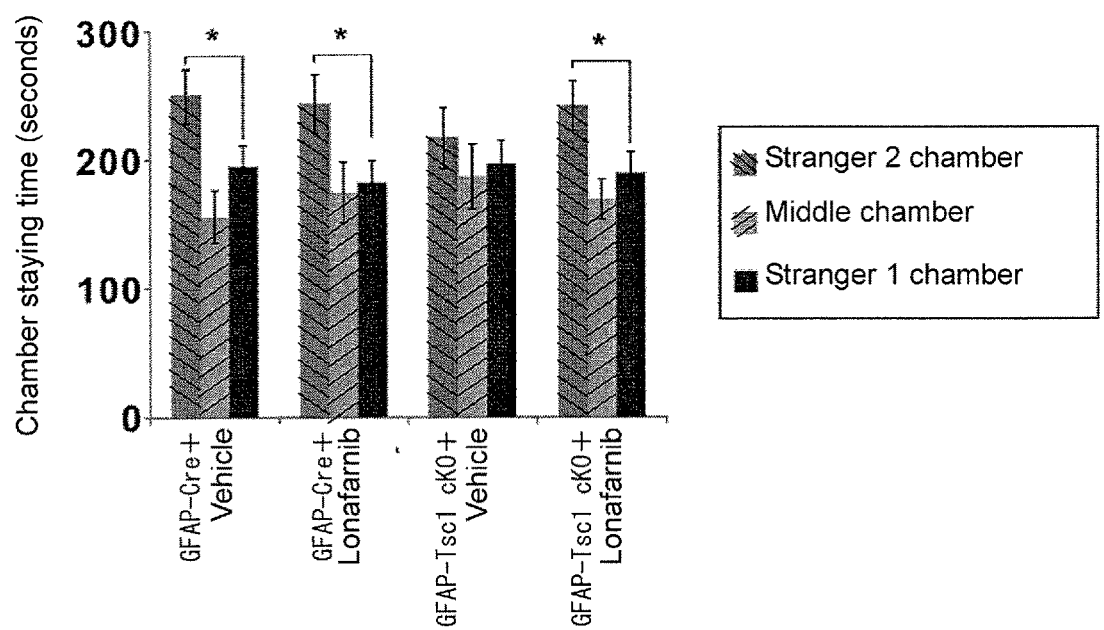
FIG. 4 is a diagram illustrating the result of the three-chamber experiment carried out in Example 2 described below, which shows a therapeutic effect of lonafarnib on mice exhibiting abnormality of social behavior (autism).

A three-chamber test was carried out in the same manner as in Example 1. In the three-chamber test, when a wild-type mouse was placed between a stranger 1 mouse and a stranger 2 mouse, the wild-type mouse stayed close to the stranger 2 for a longer time. In contrast, the GFAP-Tsc1 cKO mice did not show a significant difference between the staying times in the chambers of the stranger 1 and the stranger 2, indicating abnormality of social behavior (FIG. 4).

In view of this, single oral administration of lonafarnib (40 mg/kg, i.p.) to these mice was performed, and a three-chamber test was carried out. As a result, the staying time in the chamber of the stranger 2 became significantly longer, indicating normalization of the social behavior (FIG. 4).

The invention claimed is:

1. A method of treating autism, comprising administering an effective amount of, as an active component(s), at least one selected from the group consisting of tipifarnib and lonafarnib to a patient having said autism.

2. A method of treating memory impairment,
    comprising administering an effective amount of, as an
        active component(s), at least one selected from the group consisting of tipifarnib and lonafarnib to a patient having said memory impairment,
wherein the memory impairment is memory impairment caused by abnormality of the Tsc1 gene and/or Tsc2 gene.

3. A method of treating memory impairment, comprising administering an effective amount of, as an active component(s), at least one selected from the group consisting of tipifarnib and lonafarnib to a patient having said memory impairment,
wherein the memory impairment is epilepsy-induced memory impairment.

4. The method of claim 1, wherein said active component is tipifarnib.

5. The method of claim 1, wherein said active component is lonafarnib.

6. The method of claim 2, wherein said active component is tipifarnib.

7. The method of claim 2, wherein said active component is lonafarnib.

8. The method of claim 3, wherein said active component is tipifarnib.

9. The method of claim 3, wherein said active component is lonafarnib.

10. The method of claim 1, wherein said patient also has tuberous sclerosis.

11. The method of claim 2, wherein said patient also has tuberous sclerosis.

12. The method of claim 3, wherein said patient also has tuberous sclerosis.

13. A method of treating tuberous sclerosis, comprising administering an effective amount of, as an active component(s), at least one compound selected from the group consisting of tipifarnib and lonafarnib to a patient having said tuberous sclerosis.

14. The method of claim 13, wherein said active component is tipifarnib.

15. The method of claim 13, wherein said active component is lonafarnib.

* * * * *